United States Patent [19]

McGarry et al.

[11] 4,282,390
[45] Aug. 4, 1981

[54] 2,6-BENZYL SUBSTITUTED PHENOLS

[75] Inventors: Errol J. McGarry, Bundoora; Bruce A. Forsyth, Croydon, both of Australia

[73] Assignee: ICI Australia Limited, Melbourne, Australia

[21] Appl. No.: 25,675

[22] Filed: Mar. 30, 1979

Related U.S. Application Data

[62] Division of Ser. No. 812,471, Jul. 5, 1977, Pat. No. 4,163,801.

[30] Foreign Application Priority Data

Jul. 7, 1976 [AU] Australia .................. PC6576

[51] Int. Cl.³ ............................................. C07C 39/15
[52] U.S. Cl. ..................... 568/720; 568/640; 568/641; 568/586; 568/707
[58] Field of Search ............... 568/707, 720, 641, 640, 568/586

[56] References Cited

U.S. PATENT DOCUMENTS

| | | | |
|---|---|---|---|
| 2,713,036 | 7/1955 | Beaver et al. | 568/707 X |
| 2,735,872 | 2/1956 | Beaver et al. | 568/720 X |
| 3,067,259 | 12/1962 | Bailey | 568/640 |
| 3,076,783 | 2/1963 | Weaver | 568/720 X |
| 3,330,873 | 7/1967 | Godin et al. | 568/720 |
| 3,830,850 | 8/1974 | Stratton | 568/640 X |

OTHER PUBLICATIONS

Manecke et al, Makromol. Chem., vol. 52, (1962), pp. 147–163.
Finn et al, Jour. Applied Chem., vol. 1, (1951), pp. 524–526.
Beaver et al, (I), Jour. Amer. Chem. Soc., vol. 75, (1953), pp. 5579–5581.
Foster et al, Jour. Org. Chem., vol. 26, (1961), pp. 2539–2541.

Primary Examiner—Bernard Helfin
Attorney, Agent, or Firm—Cushman, Darby & Cushman

[57] ABSTRACT

A process for killing internal parasites of warm blooded animals which process comprises treating the infected animal with an effective amount of a composition comprising as active ingredient a compound of the general formula I:

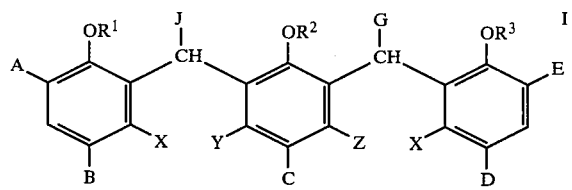

wherein $R^1$, $R^2$ and $R^3$, which may be the same or different, are hydrogen, lower alkyl, lower alkenyl, lower alkanoyl, lower alkenoyl, aroyl or $CH_2COOR^4$ wherein $R^4$ is hydrogen or lower alkyl; B, C and D, which may be the same or different, are halogen, optionally substituted lower alkyl, optionally substituted aryl, lower alkenyl, lower alkoxy, hydroxy, cyano, nitro, or $COR^5$ wherein $R^5$ is hydroxy, lower alkoxy or $NR^6R^7$ wherein $R^6$ and $R^7$, which may be the same or different, are hydrogen or lower alkyl; A, E, X, Y and Z, which may be the same or different, are hydrogen, halogen, optionally substituted lower alkyl, optionally substituted aryl, lower alkenyl, lower alkoxy, hydroxy, cyano, nitro, or $COR^5$ wherein $R^5$ is as hereinbefore defined; J and G, which may be the same or different, are hydrogen, lower alkyl, optionally substituted aryl, cyano, nitro or trichloromethyl or, together with the geminal hydrogen, the group $=CCl_2$; or an optical isomer thereof; or a salt thereof; and wherein lower alkyl and lower alkoxy are defined as groups containing from 1 to 6 carbon atoms, lower alkenyl and lower alkanoyl are defined as groups containing from 2 to 6 carbon atoms and lower alkenoyl is defined as a group containing from 3 to 6 carbon atoms; and an inert carrier therefor.

7 Claims, No Drawings

2,6-BENZYL SUBSTITUTED PHENOLS

This is a division of application Ser. No. 812,471 filed July 5, 1977 and now U.S. Pat. No. 4,163,801.

This invention relates to compositions for killing internal parasites of warm blooded animals; in particular it relates to compositions for killing trematodes or nematodes. An example of a trematode is the liver fluke (*Fasciola hepatica*) which is a parasite of bile ducts of the liver of ruminants, such as cattle, sheep and goats. The liver fluke each year causes a significant amount of economic loss, not only from the death of the host animal but also from the deterioration in the value of meat and wool produced by infected animals. In cattle a loss in milk yield from liver fluke infection will also occur and in addition the loss sustained by the condemnation of infected livers as human food may also be considerable. An example of a nematode is *Haemonchus contortus* which is a nematode parasitic in the abomasum or fourth stomach of ruminants. It is a blood sucking parasite and when present in large numbers can cause anaemia and finally the death of the host. It can cause extensive losses, not only in the value of the animals which it may kill but also in the diminished production of commercial items such as wool and meat. There is therefore a commercial need to treat animals with chemicals which are both safe and effective in reducing the incidence and severity of diseases caused by both trematodes and nematodes.

We have now found a new class of compounds which are effective in killing liver fluke.

Accordingly we provide a process for killing internal parasites of warm blooded animals which process comprises treating the infected animal with an effective amount of a composition comprising as active ingredient a compound of the general formula I:

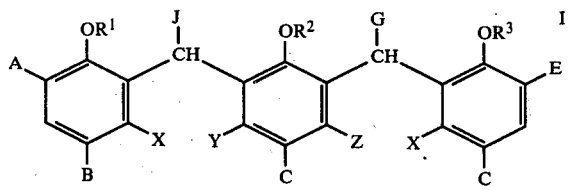

wherein $R^1$, $R^2$ and $R^3$, which may be the same or different, are hydrogen, lower alkyl, lower alkenyl, lower alkanoyl, lower alkenoyl, aroyl or $CH_2COOR^4$ wherein $R^4$ is hydrogen or lower alkyl; B, C and D, which may be the same or different, are halogen, optionally substituted lower alkyl, optionally substituted aryl, lower alkenyl, lower alkoxy, hydroxy, cyano, nitro, or $COR^5$ wherein $R^5$ is hydroxy, lower alkoxy or $NR^6R^7$ wherein $R^6$ and $R^7$, which may be the same or different, are hydrogen or lower alkyl; A, E, X, Y and Z, which may be the same or different, are hydrogen, halogen, optionally substituted lower alkyl, optionally substituted aryl, lower alkenyl, lower alkoxy, hydroxy, cyano, nitro, or $COR^5$ wherein $R^5$ is as hereinbefore defined; J and G, which may be the same or different, are hydrogen, lower alkyl, optionally substituted aryl, cyano, nitro or trichloromethyl or, together with the geminal hydrogen, the group $=CCl_2$; or an optical isomer thereof; or a salt thereof; and wherein lower alkyl and lower alkoxy are defined as groups containing from 1 to 6 carbon atoms, lower alkenyl and lower alkanoyl are defined as groups containing from 2 to 6 carbon atoms and lower alkenoyl is defined as a group containing from 3 to 6 carbon atoms; and an inert carrier therefor.

When, in the process of the invention, one or more of $R^1$, $R^2$ and $R^3$ in the compound of general formula I is aroyl suitable aroyl include, for example, benzoyl optionally substituted with one or more halogen atoms, lower alkyl, lower alkoxy, hydroxy or nitro groups.

When, in the process of the invention, one or more of A, B, C, D, E, X, Y and Z in the compound of general formula I is substituted lower alkyl suitable substituents include, for example, one or more halogen atoms, hydroxy or lower alkoxy groups.

When, in the process of the invention, one or more of A, B, C, D, E, G, J, X, Y and Z in the compound of general formula I is optionally substituted aryl, suitable aryl include, for example, phenyl optionally substituted with one or more halogen atoms, lower alkyl, lower alkoxy, hydroxy or nitro groups.

When one or more of $R^1$, $R^2$ and $R^3$ is hydrogen or $CH_2COOR^4$ wherein $R^4$ is hydrogen, one or more of A, B, C, D, E, X, Y and Z is hydroxy or $COR^5$ wherein $R^5$ is hydroxy or one or more of A, B, C, D, E, G, J, X, Y and Z is phenyl substituted with one or more hydroxy groups, the compounds of general formula I may be used in the process of the invention in a derivative form, conveniently as a salt of a pharmaceutically acceptable inorganic or organic base. Suitable bases include, for example, pharmaceutically acceptable alkali metal hydroxides, alkaline earth metal hydroxides and amines such as ammonia, triethanolamine and N-methylglutamine.

In a preferred aspect the invention provides a process as stated above wherein, in the compound of general formula I: $R^1$, $R^2$ and $R^3$, which may be the same or different, are hydrogen, lower alkyl, lower alkenyl, lower alkanoyl, lower alkenoyl, aroyl or $CH_2COOR^4$ wherein $R^4$ is hydrogen or lower alkyl; B, C and D, which may be the same or different, are halogen, lower alkyl, lower alkenyl, lower alkoxy, hydroxy, cyano, nitro or $COR^5$ wherein $R^5$ is hydroxy, lower alkoxy or $NR^6R^7$ wherein $R^6$ and $R^7$ which may be the same or different are hydrogen or lower alkyl; A, E, X, Y and Z, which may be the same or different, are hydrogen, halogen, lower alkyl, optionally substituted aryl, cyano, nitro, or $COR^5$ wherein $R^5$ is as hereinbefore defined; J and G, which may be the same or different, are hydrogen, lower alkyl, phenyl, trichloromethyl or, together with the geminal hydrogen, the group $=CCl_2$; or an optical isomer thereof; or a salt thereof; and wherein lower alkyl and lower alkoxy are defined as groups containing from 1 to 6 carbon atoms, lower alkenyl and lower alkanoyl are defined as groups containing from 2 to 6 carbon atoms and lower alkenoyl is defined as a group containing from 3 to 6 carbon atoms.

In a more preferred aspect the invention provides a process as stated above wherein, in the compound of general formula I: $R^1$, $R^2$ and $R^3$, which may be the same or different are, hydrogen, lower alkyl, lower alkanoyl or $CH_2COOR^4$ wherein $R^4$ is hydrogen or lower alkyl; B, C and D, which may be the same or different, are halogen, lower alkyl, cyano or nitro; A and E, which may be the same or different, are hydrogen, halogen, lower alkyl, cyano or nitro; X, Y and Z, which may be the same or different, are hydrogen, or halogen; J and G which may be the same or different, are hydrogen or lower alkyl; or an optical isomer thereof; or a salt thereof; and wherein lower alkyl is defined as a group containing from 1 to 6 carbon atoms and lower alkanoyl is defined as a group containing from 2 to 6 carbon atoms.

In an even more preferred aspect the invention provides a process as described above wherein, in the compound of general formula I: $R^1$, $R^2$ and $R^3$, which may be the same or different, are hydrogen or lower alkanoyl; A, B, C, D and E, which may be the same or different are halogen; X, Y and Z are hydrogen; J and G, which may be the same or different, are hydrogen or lower alkyl; or an optical isomer thereof; or a salt thereof; and wherein lower alkyl is defined as a group containing from 1 to 6 carbon atoms and lower alkanoyl is defined as a group containing from 2 to 6 carbon atoms.

In a particularly preferred aspect the invention provides a process as described above wherein, in the compound of general formula I: $R^1$, $R^2$ and $R^3$, which may be the same or different, are hydrogen or acetyl; A and E, which may be the same or different, are chlorine, bromine or iodine; B, C and D, which may be the same or different, are fluorine, chlorine or bromine; X, Y and Z are hydrogen; J and G, which may be the same or different, are hydrogen or methyl; or an optical isomer thereof; or a salt thereof.

The invention further provides a compound of general formula I, an optical isomer thereof, or a salt thereof, as hereinbefore defined wherein if C is chloro or methyl either: one or both of J and G is lower alkyl, optionally substituted aryl, cyano, nitro, trichloromethyl or, together with the geminal hydrogen, the group $=CCl_2$; or one or more of A, E, B, D, X, Y and Z is fluoro, iodo, optionally substituted $C_2$ to $C_6$ alkyl, optionally substituted aryl, lower alkenyl, lower alkoxy, hydroxy, cyano, nitro or $COR^5$ wherein $R^5$ is as hereinbefore defined.

Compounds which may be used in the process of our invention include but are by no means limited to, the following:

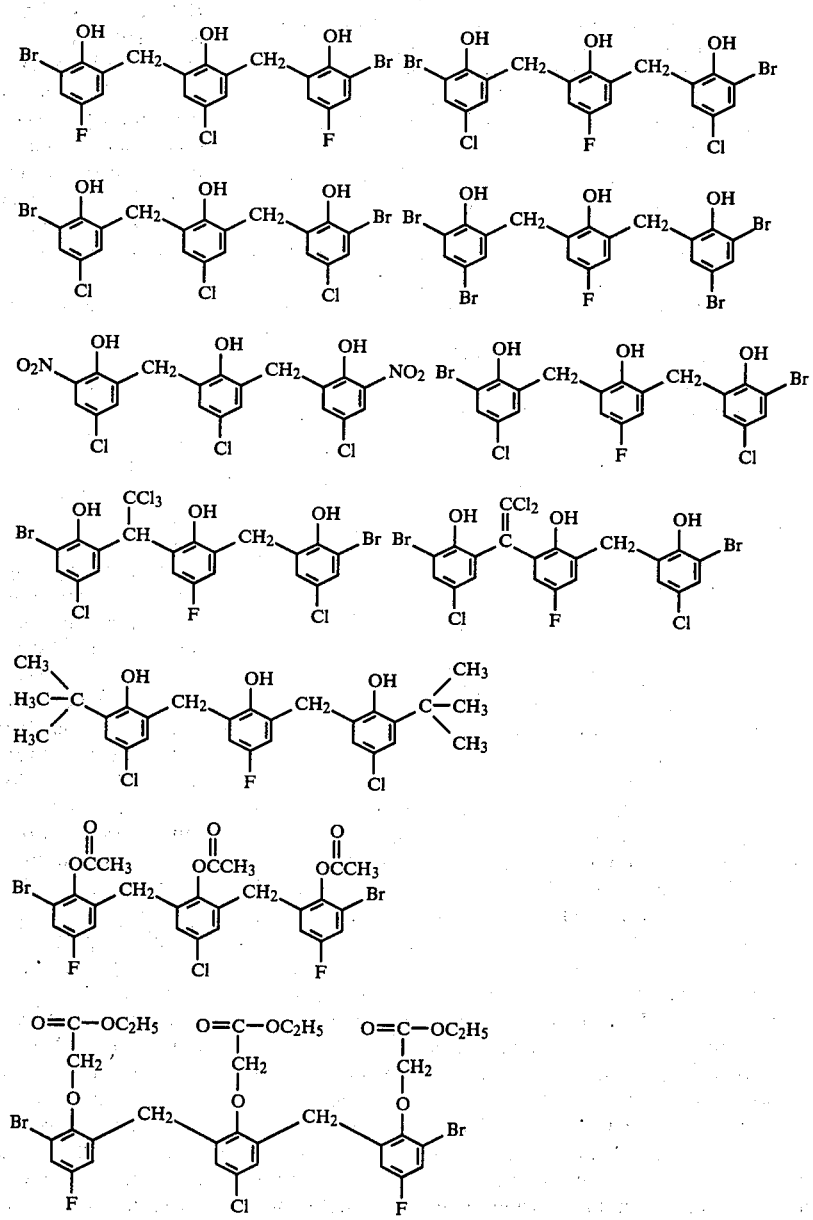

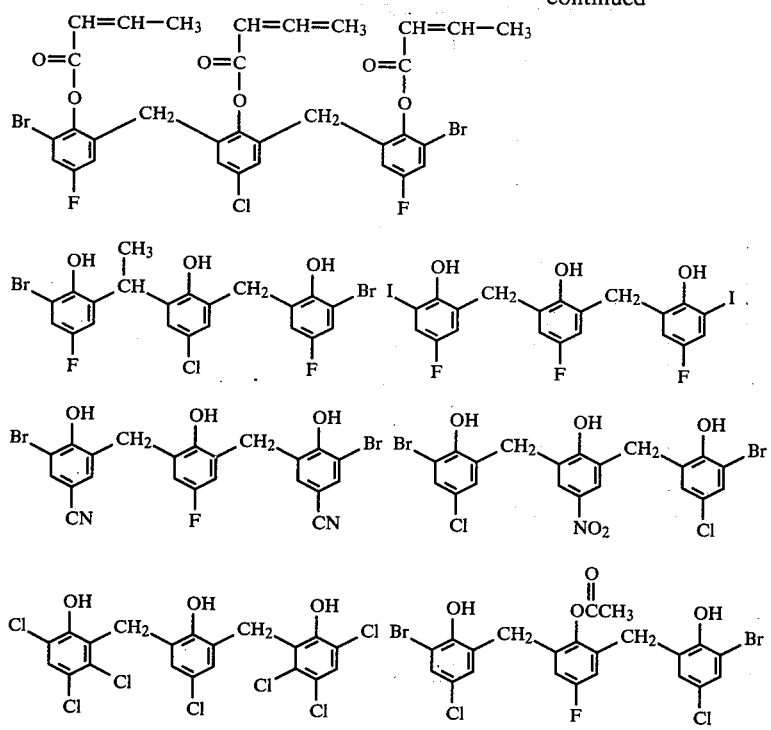

Specific examples of compounds of general formula I which may be used in the process of the invention are detailed in Table I wherein the substituents $R^1$, $R^2$, $R^3$, A, B, C, D, E, J, G, X, Y and Z refer to the substituents in the general formula I. The invention includes all those specific, novel, compounds listed in Table I.

TABLE I

| Compound No. | A | E | B | C | D | J | G | X,Y,Z | $R^1,R^2,R^3$ | m.p. °C. |
|---|---|---|---|---|---|---|---|---|---|---|
| 1 | H | H | F | Cl | F | H | H | all H | all H | 228 |
| 2 | Br | Br | F | Cl | F | H | H | all H | all H | 193 |
| 3 | H | H | Cl | F | Cl | H | H | all H | all H | 210 |
| 4 | Br | Br | Cl | F | Cl | H | H | all H | all H | 164 |
| 5 | H | H | $CH_3$ | Cl | $CH_3$ | H | H | all H | all H | 220 |
| 6 | t-Bu | t-Bu | $CH_3$ | Cl | $CH_3$ | H | H | all H | all H | 152 |
| 7 | H | H | $CH_3$ | F | $CH_3$ | H | H | all H | all H | 195 |
| 8 | t-Bu | t-Bu | $CH_3$ | F | $CH_3$ | H | H | all H | all H | 142 |
| 9 | $NO_2$ | $NO_2$ | Cl | Cl | Cl | H | H | all H | all H | 200 |
| 10 | H | H | Cl | Cl | Cl | H | H | all H | all H | 228 |
| 11 | Br | Br | Br | Cl | Br | H | H | all H | all H | 230 |
| 12 | Br | Br | Cl | Cl | Cl | H | H | all H | all H | 200 |
| 13 | Cl | Cl | Cl | Cl | Cl | H | H | all H | all H | 189 |
| 14 | Br | Br | Br | F | Br | H | H | all H | all H | 206 |
| 15 | Br | Br | Cl | Br | Cl | H | H | all H | all H | 140 |
| 16 | Br | Br | Br | Br | Br | H | H | all H | all H | 158 |
| 17 | Cl | Cl | F | Cl | F | H | H | all H | all H | 180 |
| 18 | Cl | Cl | Cl | F | Cl | H | H | all H | all H | 168 |
| 19 | Cl | Cl | Cl | Br | Cl | H | H | all H | all H | 188 |
| 20 | H | H | F | F | F | H | H | all H | all H | 198 |
| 21 | H | H | F | Br | F | H | H | all H | all H | 183 |
| 22 | Br | Br | F | F | F | H | H | all H | all H | 174 |
| 23 | Br | Br | F | Cl | F | H | H | all H | a. | 130 |
| 24 | I | I | F | Cl | F | H | H | all H | all H | 210 |
| 25 | Br | Br | F | Br | F | H | H | all H | all H | 183 |
| 26 | H | H | Br | Cl | Br | H | H | all H | all H | 234 |
| 27 | H | H | Br | F | Br | H | H | all H | all H | 225 |
| 28 | H | H | I | F | I | H | H | all H | all H | 200 |
| 29 | I | I | Cl | F | Cl | H | H | all H | all H | b. |
| 30 | Cl | Br | Cl | F | Cl | $CH_3$ | H | all H | all H | 171 |
| 31 | Br | Br | Cl | F | Cl | H | H | all H | c. | 206 |
| 32 | Br | Br | Cl | F | Cl | $CH_3$ | H | all H | all H | 150 |
| 33 | Br | Br | Cl | F | Cl | H | H | all H | d. | 75 |
| 34 | $NO_2$ | $NO_2$ | Cl | F | Cl | H | H | all H | all H | b. |
| 35 | Br | H | Cl | F | Cl | $CH_3$ | H | all H | all H | 174 |
| 36 | Cl | H | Cl | F | Cl | $CH_3$ | H | all H | all H | 166 |
| 37 | t-Bu | t-Bu | Cl | F | Cl | H | H | all H | all H | b. |
| 38 | I | I | F | F | F | H | H | all H | all H | 202 |
| 39 | Br | Br | F | Cl | F | $CH_3$ | H | all H | all H | 156 |

TABLE I-continued

| Compound No. | A | E | B | C | D | J | G | X,Y,Z | R¹,R²,R³ | m.p. °C. |
|---|---|---|---|---|---|---|---|---|---|---|
| 40 | Br | Br | F | Cl | F | $CH_3$ | $CH_3$ | all H | all H | 136 |
| 41 | Br | Br | F | Cl | F | H | H | e. | all H | 226 |
| 42 | Br | Br | F | Cl | F | H | H | all H | f. | 181 |
| 43 | Br | Br | F | Cl | F | H | H | all H | g. | 86 |
| 44 | H | H | F | Cl | F | H | H | e. | all H | 176 |
| 45 | Br | H | F | Cl | F | $CH_3$ | H | all H | all H | b. |
| 46 | Cl | Br | Cl | F | F | $CH_3$ | H | all H | all H | 171 |
| 47 | Cl | H | Cl | F | F | $CH_3$ | H | all H | all H | 158 |
| 48 | Br | Br | Cl | Cl | Cl | H | H | e. | all H | 192 |
| 49 | I | I | Cl | Cl | Cl | H | H | all H | all H | 184 |
| 50 | Cl | Cl | Cl | Cl | Cl | H | H | h. | all H | 228 |
| 51 | Br | Br | Cl | Cl | Cl | H | H | all H | f. | b. |
| 52 | Br | Br | Cl | Cl | Cl | H | H | all H | g. | 100 |
| 53 | H | H | Cl | Cl | Cl | H | H | e. | all H | 148 |
| 54 | I | I | Cl | Br | Cl | H | H | all H | all H | 192 |
| 55 | I | I | Br | Cl | Br | H | H | all H | all H | 200 |
| 56 | Br | Br | Cl | F | Cl | H | H | all H | a. | 130 |
| 57 | Br | Br | Cl | F | Cl | H | H | all H | f. | 224 |
| 58 | Br | Br | Cl | F | Cl | H | H | all H | g. | 88 |
| 59 | Br | Br | Cl | $NO_2$ | Cl | H | H | all H | all H | 224 |
| 60 | Br | Br | $NO_2$ | F | $NO_2$ | H | H | all H | all H | 248 dec. |
| 61 | H | H | $NO_2$ | F | $NO_2$ | H | H | all H | all H | 224 |
| 62 | Br | Br | CN | F | CN | H | H | all H | all H | 240 |
| 63 | H | H | CN | F | CN | H | H | all H | all H | 222 |
| 64 | Br | Br | $CO_2H$ | Cl | $CO_2H$ | H | H | all H | all H | 200 dec. |
| 65 | Br | Br | $CO_2H$ | Cl | $CO_2H$ | H | H | all H | a. | 240 dec. |
| 66 | Br | Br | $CO_2CH_3$ | Cl | $CO_2CH_3$ | H | H | all H | all H | 160 |
| 67 | H | H | $CO_2CH_3$ | Cl | $CO_2CH_3$ | H | H | all H | all H | b. |
| 68 | Br | Br | $CO_2CH_3$ | F | $CO_2CH_3$ | H | H | all H | all H | 212 |
| 69 | H | H | $CO_2CH_3$ | F | $CO_2CH_3$ | H | H | all H | all H | 236 |
| 70 | Br | Br | $CO_2CH_3$ | $CO_2CH_3$ | $CO_2CH_3$ | $CH_3$ | $CH_3$ | all H | all H | b. |
| 71 | H | H | $CO_2CH_3$ | $CO_2CH_3$ | $CO_2CH_3$ | $CH_3$ | $CH_3$ | all H | all H | 180 |
| 72 | H | H | Br | Br | Br | H | H | all H | all H | b. |
| 73 | H | H | Br | Br | Br | H | H | all H | a. | b. |
| 74 | H | H | Br | Cl | Br | H | H | e. | all H | 228 |
| 75 | H | H | I | Cl | I | H | H | all H | all H | 194 |
| 76 | H | H | F | Cl | F | $CH_3$ | $CH_3$ | all H | all H | 224 |
| 77 | H | H | $CH_3$ | $CH_3$ | $CH_3$ | H | H | all H | a. | 124 |
| 78 | H | H | $CH_3$ | $CH_3$ | $CH_3$ | H | H | all H | all H | 216 |
| 79 | H | H | Cl | $NO_2$ | Cl | H | H | all H | all H | 220 | a. all $COCH_3$
b. m.p. not determined
c. $R^1 = R^3 = H$; $R^2 = COCH_3$
d. all $CH_3$
e. $X = Y = H$; $Z = Cl$
f. all $CH_2CO_2H$
g. all $CH_2CO_2C_2H_5$
h. $Y = Z = H$; $X = Cl$ In the foregoing Table the following groups of Compounds are preferred groups but are progressively less preferred groups moving from group (i) through to group (iii).
(i) 2, 4, 22, 29, 38, 39
(ii) 14, 18, 24, 25, 30, 31, 46
(iii) 9, 17, 40

All these compounds are new and, in particular as grouped, form preferred aspects of the present invention; together with processes using them to combat internal parasites of warm blooded animals; compositions containing them; and new and/or analogous processes herein described for making them.

The compounds of general formula I useful in the process of the invention, both novel and known, can be made either by:

(a) condensation of two moles of a para-substituted phenol or phenolic derivative thereof and one mole of a para-substituted-2,6-bis(1-hydroxyalkyl) phenol or phenolic derivative thereof;

(b) condensation of two moles of a para-substituted-2-(1-hydroxyalkyl)phenol or phenolic derivative thereof and one mole of a para-substituted phenol or phenolic derivative thereof;

(c) condensation of two moles of a para-substituted phenol or phenolic derivative thereof and one mole of a para-substituted-2,6-bis(1-haloalkyl)phenol or phenolic derivative thereof;

(d) condensation of two moles of a para-substituted-2-(1-haloalkyl)phenol or phenolic derivative thereof and one mole of a para-substituted phenol or phenolic derivative thereof;

(e) subjecting a compound of general formula I, prepared as described above under (a), (b), (c) or (d), wherein one or both of A and E is hydrogen, to an electrophilic aromatic substitution reaction, or (f) treating a compound of general formula I, prepared as described above under (a), (b), (c) or (d), wherein one or more of $R^1$, $R^2$ and $R^3$ is hydrogen with a reagent to replace one or more of said hydrogen and prepare a phenolic derivative of said compound.

Compounds of general formula I wherein A and E are the same substituent (IV) may be prepared, for example, by the acid catalysed condensation of two moles of the appropriate para-substituted phenol (II) and one mole of the appropriate para-substituted 2,6-bis(1-hydroxyalkyl)phenol (III).

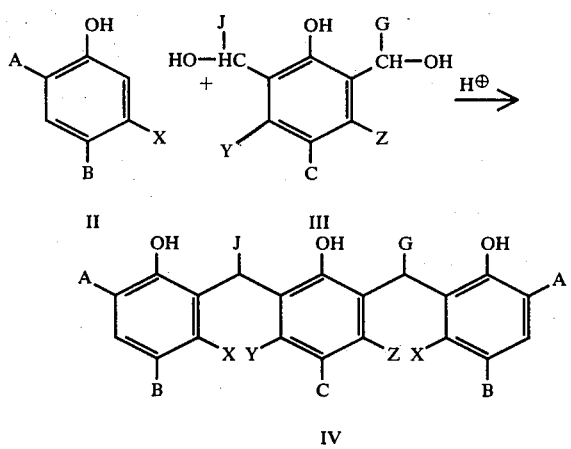

Compounds of general formula I wherein A and E are different and B and D are different may be prepared in a similar manner by a two step condensation process. An alternative method of preparation of certain of the compounds of general formula IV is by electrophilic aromatic substitution (for example halogenation or nitration) of the appropriately substituted 2,6-bis(2-hydroxybenzyl)phenol.

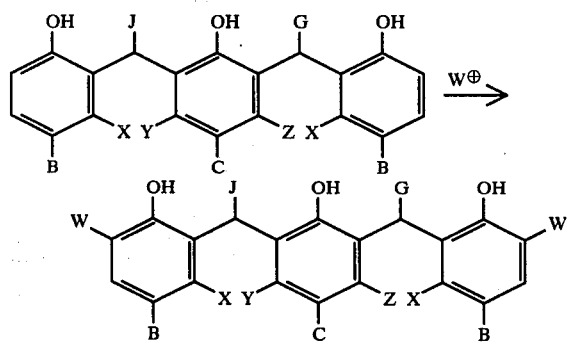

Compounds of general formula I wherein one or more of $R^1$, $R^2$ and $R^3$ are not hydrogen may be prepared from the corresponding phenols of general formula I by methods known to those skilled in the art for the preparation of phenolic derivatives. Alternatively certain of these compounds may be prepared by the acid catalysed condensation of the phenolic derivatives of the appropriate phenol and para-substituted 2,6-bis(1-hydroxyalkyl)phenol.

In the process of our invention the compounds may be used on their own but are preferably used in the form of a composition which comprises an inert carrier.

The compositions are of particular use for the treatment of Fasciola sp such as, for example, *Fasciola hepatica* and *Fasciola gigantica*.

For effective treatment, certain dosage levels are required depending upon the compound employed, the type of animal to be treated, and the particular helminth being combatted. In general, efficacy against fluke is achieved when the composition is administered in a single dose at dosage levels of from about 1 to 50 mg active ingredient/kg of animal body weight, and preferably from about 1 to 20 mg active ingredient per kg of animal body weight.

The compositions of the present invention may be administered in a variety of ways, depending upon the particular animal employed, the type of anthelmintic treatment normally given to such an animal, the materials employed, and the particular helminths being combatted. It is preferred to administer them in a single efficacious oral or parenteral dose at a time when fluke or nematode infection is apparent or suspected. They may be employed alone or in combination with other anthelmintics, parasiticides or antibacterials. The compounds may also be applied as a "pour on" formulation for dermal application. The amounts of the active anthelmintic ingredient in the composition, as well as the remaining constituents, are varied according to the type of treatment to be employed, the host animal, and the particular parasitic disease being treated. In general, however, compositions containing a total weight percent of the active compound or compounds ranging from 0.001 to 95% will be suitable with the remainder being any suitable carrier or vehicle. Furthermore, the compositions should contain enough of the active ingredient to provide an effective dosage for the proper treatment of the parasitic disease.

A number of modes of treatment may be employed, and each to some extent determines the general nature of the composition. For example, the anthelmintic compositions may be administered to domesticated animals in single unit oral dosage form such as a tablet, bolus, capsule or drench; in a liquid form suitable for parenteral administration; or they may be compounded as feed premix to be later admixed with the animal's food.

When the compositions are to be solid unit dosage forms as in tablets, capsules, or boluses, the ingredients other than the active ingredient may be any other pharmaceutically acceptable vehicles convenient in the preparation of such forms, and preferably materials nutritionally suitable such as starch, lactose, talc, magnesium stearate, vegetable gums, and the like. Moreover when capsules are employed, the active compound may be used in essentially undiluted form, the only extraneous material being that of the capsule casing itself which may be hard or soft gelatin or any other pharmaceutically acceptable encapsulating material. When the dosage form is to be used for parenteral administration, the active material is suitably admixed with an acceptable base vehicle. In all of such forms, i.e. in tablets, boluses, capsules, and injectable formulations, the active compound conveniently ranges from about 5 to 80% by weight of the total composition.

When the unit dosage form is to be in the form of a drench, the active ingredient may be mixed with agents which will aid in the subsequent suspending of the active compound in water, such as bentonite, clays, water-soluble starch, cellulose derivatives, gums, surface active agents and the like to form a dry predrench composition, and this predrench composition added to water just before use. In the predrench formulation, in addition to the suspending agent, such ingredients as preservatives, antifoam compounds, and the like may be employed. Such a dry product may contain as much as 95% by weight of the active compound the rest being contributed by the excipients. Preferably, the solid composition contains from 30% to 95% by weight of the active compound. Enough water should be added to the solid product to provide the proper dosage level within a convenient amount of liquid for a single oral dose. Liquid drench formulations containing from about 10 to 50 weight percent of dry ingredients will in general be suitable with the preferred range being from 15 to 30 weight percent.

Where the compositions are intended to be used as feeds, feed supplements, or feed premixes, they will be mixed with suitable ingredients of an animal's nutrient ration. The solid orally-ingestible carriers normally used for such purposes, such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone and the like are all suitable. The active compounds are intimately dispersed or admixed throughout the solid inert carrier by methods such as grinding, stirring, milling or tumbling. By selecting proper diluents and by altering the ratio of carrier to active ingredient, compositions of any desired concentration may be prepared. Feed supplement formulations containing from about 10 to 30% by weight of active ingredient are particularly suitable for addition of feeds. The active compound is normally dispersed or mixed uniformly in the diluent but in some instances may be adsorbed on the carrier.

These supplements are added to the finished animal feed in an amount adequate to give the final concentration of active ingredient desired for controlling or treating the helminth infection by way of the animal ration. Although the preferred level in feeds will depend on the particular compounds being employed, the active ingredients of this invention are normally fed at levels of 0.05–25% in the feed. As stated above, animals are preferably treated at a time when the infestation is apparent or suspected and the most preferred method for such treatment is via the single oral dose technique. Thus administration of medicated feed is not preferred but may certainly be employed. Similarly, the amounts of drug present in the feed may be reduced to levels in the order of 0.001% to 3.0 weight percent based on the weight of feed, and the medicated feed administered over prolonged periods. This would be in the nature of a preventive or propylactic measure but again is not the mode of choice. Another method of administering the compositions of this invention to animals whose feeds are conveniently pelleted, such as sheep, is to incorporate them directly in the pellets. For instance, the compositions are readily incorporated in nutritionally adequate alfalfa pellets at levels of 2 to 110 grams per pound of pellets for therapeutic use, and at lower levels for example 80 to 1000 milligrams per pound for prophylactic use, and such pellets fed to the animals. The compositions may also optionally contain other drugs of veterinary utility. Veterinary drugs which may be present in the veterinary compositions of this invention, depending upon the mode of administration of the said compositions, include for example, piperazine, 1-diethyl-carbamyl-4-methyl-piperazine, tetrachloroethylene, organic and inorganic arsenical compounds, tetramisole, 2-phenyl-benzimidazole, thiabendazole, phenothiazine, mebendazole and pyrantel salts.

The compositions may be administered to the animal by parenteral dose and in a further aspect of our invention we provide an injectable composition comprising a sterile solution containing from 5 to 70% w/w preferably 5 to 50% w/w of the active ingredient in a pharmaceutically acceptable solvent. The composition may be sterilized by methods known to those skilled in the art for the sterilization of injectable solution such as, for example, ultra filtration or gamma radiation.

The compositions may also be administered by application to the skin of the animal and in yet a further aspect the invention provides a liquid composition for external application to an animal said composition comprising a solution or suspension containing from 1 to 70% w/w preferably 1 to 10% w/w of the active ingredient in a pharmaceutically acceptable liquid carrier. Suitable liquid carriers include, for example, pharmaceutically acceptable hydrocarbons, ketones, esters, ethers, alcohols, amides, sulphones and sulphoxides.

The invention is now illustrated by, but by no means limited to, the following examples in which all parts are part by weight and all temperatures are in degrees Centigrade unless otherwise specified.

EXAMPLE 1

4-Chloro-2,6-bis(5-fluoro-2-hydroxybenzyl)phenol (1)

A mixture of 4-chloro-2,6-bis(hydroxymethyl)phenol (4.8 g), 4-fluorophenol (16.0 g), benzene (25 ml) and hydrochloric acid (5 drops) was heated on a boiling water bath until all the benzene had evaporated. On cooling the mixture deposited colourless crystals of 4-chloro-2,6-bis(5-fluoro-2-hydroxybenzyl)phenol (11.9 g), mp 228° C.

Compounds No. 5, 6, 15, 19, 21, 26, 44, 53, 54, 67, 72 74 and 75 of Table I were prepared by condensation of an appropriately substituted 2,6-bis(hydroxymethyl)-phenol with an appropriately substituted phenol by an analogous procedure to that described above for the preparation of compound No. 1.

EXAMPLE 2

2,6-bis(3-bromo-5-fluoro-2-hydroxybenzyl)-4-chlorophenol (2)

A solution of bromine (0.55 ml) in acetic acid (10 ml) was added dropwise to a solution of 4-chloro-2,6-bis(5-fluoro-2-hydroxybenzyl)phenol (2.0 g) in glacial acetic acid (25 ml). After 1 hr the solid which precipitated was filtered and crystallised from dilute acetic acid to give 2,6-bis(3-bromo-5-fluoro-2-hydroxybenzyl)-4-chlorophenol (2.4 g), mp 192°–4° C.

Compounds No. 12, 16, 17, 24, 25, 41, 49, 55 and 66 of Table I were prepared by halogenation of compounds No. 10, 72, 1, 1, 21, 1, 10, 26 and 67 respectively by a process analogous to that described above for the preparation of compound No. 2.

EXAMPLE 3

2,6-bis(5-chloro-2-hydroxybenzyl)-4-fluorophenol (3)

Formalin (37%, 110 ml) was added dropwise to a solution of p-fluorophenol (56 g) and sodium hydroxide (25 g) in water (60 ml) at a temperature of 15° C. and then the mixture was allowed to stand for 7 days. During this period crystals were deposited. The mixture was diluted with 15% brine solution (120 ml) and the crystal cake was crushed and stirred until fairly uniform. The solid was filtered and washed with 15% brine solution (80 ml). The solid collected was then dissolved in water and precipitated with dilute acetic acid. After filtration the product crystallised from methanol as colourless prisms of 4-fluoro-2,6-bis(hydroxymethyl) phenol (38.2 g); mp 144° C.

A mixture of p-chlorophenyl (20 g); 4-fluoro-2,6-bis (hydroxymethyl)phenol (4.8 g), benzene (50 ml) and concentrated hydrochloric acid (5 drops) was heated on a boiling water bath for 1 hour. On cooling colourless crystals of 2,6-bis(5-chloro-2-hydroxybenzyl)-4-fluorophenol (9.6 g) were obtained, mp 210° C.

Compounds No. 7, 20, 27, 28 and 69 of Table I were prepared by a process analogous to that described above for the preparation of compound No. 3.

EXAMPLE 4

2,6-bis(3-bromo-5-chloro-2-hydroxybenzyl)-4-fluorophenol (4)

2,6-bis(5-chloro-2-hydroxybenzyl)-4-fluorophenol was brominated following the procedure described in Example 2, to give 2,6-bis(3-bromo-5-chloro-2-hydroxybenzyl)-4-fluorophenol, mp 164° C.

Compounds No. 14, 18, 22, 29, 38 and 68 of Table I were prepared by halogenation of compounds No. 27, 3, 20, 3, 20 and 69 respectively by a process analogous to that described above for the preparation of compound No. 4.

EXAMPLE 5

2,6-bis(3,5-dichloro-2-hydroxybenzyl)-4-fluorophenol (18)

4-fluoro-2,6-bis(hydroxymethyl)phenol (2.0 g) was dissolved in glacial acetic acid (20 ml) and added slowly to 2,4-dichlorophenol (3.8 g) in concentrated $H_2SO_4$ at 60°–70°. The mixture was held at 65°–70° for 1 hr, cooled, acetic acid (20 ml) was added to dissolve the solids and the solution was poured into ice-water. The solid precipitate was purified by column chromatography over silica gel using hexane-ethyl acetate as eluent. The title compound was obtained in yield of 1.3 g, mp 168°.

Compounds No. 8 and 37 of Table I were also prepared by a process analogous to that described above for the preparation of compound no 18.

EXAMPLE 6

2,6-bis(5-chloro-2-hydroxybenzyl)-4-nitrophenol (79)

To a mixture of p-nitrophenol (27.8 g) and $ZnCl_2$ (5 g) was added 200 ml of chloromethyl methyl ether. The solution was heated under reflux for 8 hrs. Excess choromethyl methyl ether was removed in vacuo and the dry solid was recrystallized from benzene and hexane to give white crystals of 2,6-bis(chloromethyl)-4-nitrophenol.

The 2,6-bis(chloromethyl)-4-nitrophenol (8 g) and p-chlorophenol (8.7 g) were dissolved in nitrobenzene (125 ml) at 25°. After cooling to 10° $ZnCl_2$ (28 g) was added over 1 hr. The stirred mixture was held at room temperature for 30 hrs and poured into 200 mls of water. The organic layer was washed with water and the nitrobenzene removed by vacuum distillation. Column chromatography gave 1.5 g of 2,6-bis(5-chloro-2-hydroxybenzyl)-4-nitrophenol (mp 220°).

EXAMPLE 7

2,6-Bis(3-bromo-5-chloro-2-hydroxybenzyl)-4-nitrophenol (59)

2,6-Bis(5-chloro-2-hydroxybenzyl)-4-nitrophenol was brominated using bromine in tetrahydrofuran-carbon tetrachloride. The title compound was obtained as a crystalline solid m.p. 240°.

EXAMPLE 8

2,6-Bis(5-cyano-2-hydroxybenzyl)-4-fluorophenol (63)

4-Fluoro-2,6-bis(hydroxymethyl)phenol (25 g; mp 144°) was added to 33% w/v aqueous hydrochloric acid (100 ml). After stirring at room temperature for 10 min all the solid dissolved. A flocculent white precipitate formed soon after. The precipitate was collected by filtration, dried and recrystallized from cyclohexane to give 2,6-bis(chloromethyl)-4-fluorophenol (19.5 g, mp 70°).

p-Cyanophenol (19.4g) and 2,6-bis(chloromethyl)-4-fluorophenol (17.0 g) were dissolved in nitrobenzene (250 ml) at 20°. The solution was cooled to 10° and crushed aluminium chloride (anhydrous 65 g) was added in 5 g portions over two hours. During the addition the temperature was maintained at 10°–12°. Stirring was continued at 20° for 14 hrs. The viscous black mixture was poured onto a vigorously stirred mixture of ice (2 l) and dichloro methane (2 l). The organic solvent layer was dried, dichloro methane and nitrobenzene removed by vacuum distillation and the residual tar passed through a silica column. The product, 2,6-bis(5-cyano-2-hydroxybenzyl)-4-fluorophenol (mp 222°) was obtained in 3% yield.

Compound No. 61 of Table I was prepared by a process analogous to that described above for the preparation of compound No. 63.

EXAMPLE 9

2,6-Bis(3-bromo-5-cyano-2-hydroxybenzyl)-4-fluorophenol (62)

A stirred suspension of 2,6-bis(5-cyano-2-hydroxybenzyl)-4-fluoro phenol (0.6 g) in glacial acetic acid (10 ml) was treated with bromine (0.56 g) in 5 ml glacial acetic acid for 24 hrs at room temperature. The white solid from the reaction mixture was washed with acetic acid and hexane to give 2,6-bis(3-bromo-5-cyano-2-hydroxybenzyl)-4-fluorophenol (0.6 g, mp 240°).

Compound No. 60 of Table I was prepared by a process analogous to that described above for the preparation of compound No. 62.

EXAMPLE 10

2,6-Bis(5-chloro-2-hydroxy-3-nitrobenzyl)-4-chlorophenol (9)

4-Chloro-2,6-bis(hydroxymethyl)phenol (25 g, m.p. 162°) was added to 33% aqueous hydrochloric acid (100 ml). After stirring for 3 hr the white precipitate was collected, dried and recrystallised from cyclohexane to give 2,6-bis(chloromethyl)-4-chlorophenol (18 g, m.p. 88°).

Zinc chloride (2 g) was added in small portions over 75 min to a melt of 2,6-bis(chloromethyl)-4-chlorophenol (1.2 g) and 4-chloro-2-nitrophenol (3 g) at a temperature of 120°. The mixture was stirred at this temperature for approximately 1 hr. The black product was extracted several times with acetone and the extract filtered to remove black inorganic material. The acetone was removed by distillation under reduced pressure and the residue chromatographed on silica gel. Elution with hexane containing 3% ethyl acetate gave unreacted 4-chloro-2-nitrophenol and elution with hexane containing 20% ethyl acetate gave the title compound (0.5 g) which was recrystallised from aqueous ethanol; m.p. 200°.

EXAMPLE 11

2-(5-chloro-2-hydroxybenzyl)-6-[1-(3,5-dichloro-2-hydroxyphenyl)ethyl]-4-fluorophenol (36)

Powdered anhydrous aluminium chloride (100 g) was added to 2,4-dichloro-phenyl acetate at room temperature with stirring. The temperature was increased to 150°–160° for 40 min. Treatment of the reaction mixture with ice-water and hydrochloric acid gave 3,5-dichloro-2-hydroxy-acetophenone (63 g, m.p. 99°).

3,5-Dichloro-2-hydroxyacetophenone (40 g) was treated in ethanol with sodium borohydride (4 g). The solid reaction product was recrystallized from benzene to give 2,4-dichloro-6-(1'-hydroxy ethyl) phenol (32 g, m.p. 70°).

2,4-Dichloro-6-(1'-hydroxyethyl)phenol (10 g) was added in small portions to a melt of 4-fluoro phenol containing a trace of p-toluenesulphonic acid at 90° over a half hour period. The reaction mixture was stirred for a further ½ hr and cooled. The crystallization from benzene gave 1-(3,5-dichloro-2-hydroxyphenyl)-1-(5-fluoro-2-hydroxy phenyl) ethane (11 g, m.p. 150°).

1-(3,5-Dichloro-2-hydroxyphenyl)-1-(5-fluoro-2-hydroxyphenyl) ethane (3 g) was dissolved in aqueous sodium hydroxide solution (5 ml, 16% w/v) and added dropwise to formalin (3 ml, 40%) at 80° and stirred for 2 hrs at this temperature. After treatment with iced water and hydrochloric acid the product was isolated and recrystallized from ethyl acetate to give 1-(3,5-dichloro-2-hydroxyphenyl)-1-(5-fluoro-2-hydroxy-3-hydroxy methyl phenyl) ethane (m.p. 148°) 2.2 g.

p-Chlorophenol (2.5 g) was heated to 60° and a trace of p-toluenesulphonic acid added. The 1,1-diphenylethane obtained above (1.5 g) was added slowly to the melt. After the addition was complete, benzene (50 ml) was added and the solution was heated under reflux for 14 hrs to remove water from the reaction mixture. The product was purified by column chromatography to give 2-(5-chloro-2-hydroxy-benzyl)-6-[1-(3,5-dichloro-2-hydroxyphenyl) ethyl]-4-fluorophenol (1.1 g m.p. 166°).

Compounds No. 35, 45 and 47 of Table I were prepared by an analogous process to that described above for the preparation of compound No. 36.

EXAMPLE 12

2-(3-Bromo-5-chloro-2-hydroxybenzyl)-6-[1-(3,5-dichloro-2-hydroxyphenyl)ethyl]-4-fluorophenol (30)

2-(5-Chloro-2-hydroxybenzyl)-6-[1-(3,5-dichloro-2-hydroxyphenyl) ethyl]-4-fluorophenol was brominated using bromine in acetic acid at room temperature to give the title compound; m.p. 171°.

Compounds No. 32, 39 and 46 of Table I were prepared from compounds 35, 45 and 47 respectively by a process analogous to that described above for the preparation of compound No. 30 from compound No. 36.

EXAMPLE 13

4-Chloro-2,6-bis[1-(5-fluoro-2-hydroxyphenyl)ethyl]-phenol (76)

Sodium borohydride was added in small portions to a methanolic solution of 4-chloro-2,6-diacetylphenol (5 g) until the colour was completely discharged. The solvent was removed by distillation under reduced pressure to give a white solid which was washed with water and dilute hydrochloric acid. The product, 2,6-bis(1-hydroxyethyl)-4-chlorophenol, was obtained as a pale yellow gum (4.5 g).

A mixture of 2,6-bis(1-hydroxyethyl)-4-chlorophenol (2 g) and 4-fluorophenol (2 g) was heated under reflux in benzene (50 ml) containing a catalytic amount of p-toluenesulphonic acid. On standing overnight at room temperature the title compound (1.3 g) crystallised; m.p. 224°.

Compound No. 71 of Table I was prepared by a procedure analogous to that described above for the preparation of compound No. 76.

EXAMPLE 14

2,6-Bis[1-(3-bromo-5-fluoro-2-hydroxyphenyl)ethyl]-4-chlorophenol (40)

A solution of bromine (0.35 ml) in glacial acetic acid (5 ml) was added dropwise to a solution of 4-chloro-2,6-bis[1-(5-fluoro-2-hydroxyphenyl)ethyl]phenol (1.3 g) in glacial acetic acid (30 ml) and the solution was stirred at room temperature for 2 hr. The solution was then poured into water and the pale yellow solid was washed well with water and then crystallised from hexane to give the title compound (0.6 g), m.p. 136°.

Compound No. 70 of Table I was prepared by the bromination of compound No. 71 by a procedure analogous to that described above for the preparation of compound No. 40.

EXAMPLE 15

2,6-Bis(3-bromo-5-chloro-2-methoxybenzyl)-4-fluoroanisole (33)

A mixture of 2,6-bis(3-bromo-5-chloro-2-hydroxybenzyl)-4-fluorophenol (10 g), potassium carbonate (10 g) and dimethyl sulphate (7 g) in acetone (250 ml) was heated under reflux for 12 hr. The title compound was isolated and purified by column chromatography; m.p. c. 75°.

EXAMPLE 16

Compound No. 64 of Table I was prepared from compound No. 66 by based catalysed ester hydrolysis.

EXAMPLE 17

Compounds No. 23, 56, 65, 73 and 77 of Table I were prepared by esterification of the phenols. compounds No. 2, 4, 64, 72 and 78 respectively, using acetic anhydride.

EXAMPLE 18

Compounds No. 43, 52 and 58 of Table I were prepared by esterification of the phenols, compounds No. 2, 4 and 12 respectively, using ethyl chloroacetate.

EXAMPLE 19

Compounds No. 42, 51 and 57 were prepared by hydrolysis of the alkyl ester moiety of compounds No. 43, 52 and 58 respectively.

EXAMPLE 20

Compound No. 31 was prepared by mono-esterification of compound No. 4 using a molar quantity of acetic anhydride.

EXAMPLE 21

Compositions suitable for use as experimental aqueous oral drenches were prepared in the following general manner. A mixture of the required amount of active ingredient was mixed with 40 ml of an aqueous 0.25% w/w solution of "Lubrol E" ("Lubrol E" is a Registered Trade Mark for an octylphenol ethoxylate). The mixture was ball-milled for 30 minutes and the resultant suspension was used as an aqueous drench.

EXAMPLE 22

Compositions suitable for use as experimental injectable solutions were prepared by dissolving the chemical in propylene glycol and adjusting the concentration to 10% w/v active ingredient.

EXAMPLE 23

Compositions prepared by the methods of Examples 21 and 22 were used as a single dose to test sheep infected with sheep lever fluke (*Fasciola hepatica*). The number of liver fluke eggs in the faeces was measured at the time of treatment and at selected intervals up to 14 days after treatment. The sheep were killed on day 14 and the number of adult fluke in the liver counted. The amount and structure of active ingredient in each composition and the results of treatment of a sheep with that composition are given in the Table II below. The compositions were administered either by oral drench (oral) or by sub-cutaneous injection (s/c).

TABLE II

FLUKICIDAL ACTIVITY OF COMPOSITIONS COMPRISING AS ACTIVE INGREDIENT A COMPOUND OF GENERAL FORMULA I

| Active Ingredient Compound No. | Dose Rate (mg/kg) | Route | Faecal Egg Count Eggs per g faeces (day) | Post Mortem Results No. of adult fluke |
|---|---|---|---|---|
| 2 | 12.5 | s/c | 1800(0), 3800(3), 0(7), 0(14) | 0 |
| 2 | 12.5 | oral | 340(0), 130(2), 0(7), 0(13) | 0 |
| 2 | 6.5 | oral | 500(0), 40(7), 0(14) | 0 |
| 2 | 3.1 | oral | 300(0), 20(7), 0(14) | 0 |
| 4[a] | 12.5 | oral | 140(0), 2520(2), 200(7), 0(14) | 0 (Day 29) |
| 4 | 6.3 | oral | 230(0), 70(2), 0(7) | 0 |
| 4 | 3.1 | oral | 170(0), 0(2), 10(7), 0(14) | 0 |
| 4 | 2.0 | oral | 2000(0), 110(7), 10(14) | 0 |
| 4 | 1.0 | oral | 500(0), 10(7), 150(14) | — |
| 4 | 2.0 | s/c | 80(0), 20(7), 0(14) | 0 |
| 22 | 12.5 | oral | 430(0), 1340(7), 0(14) | 0 |
| 22 | 6.3 | oral | 350(0), 0(7), 0(14) | 0 |
| 29[b] | 12.5 | oral | 340(0), 10(7), 0(14) | |
| 29 | 6.3 | oral | 170(0), 0(7), 0(14) | 0 |
| 38 | 6.3 | oral | 430(0), 190(7), 0(14) | 0 |
| 38 | 4.0 | oral | 470(0), 50(7), 80(14) | |
| 39 | 6.0 | oral | 750(0), 60(7), 0(14) | 0 |
| 39 | 3.0 | oral | 480(0), 210(7), 0(14) | 0 |
| 12 | 12.5 | oral | 220(0), 40(7), 0(14) | 0 |
| 12 | 4.0 | oral | 160(0), 0(7), 0(14) | 0 |
| 14 | 12.5 | oral | 200(0), 60(7), 0(14) | 0 |
| 14 | 4.0 | oral | 10(0), 0(7), 0(14) | 1 |
| 18 | 12.5 | oral | 430(0), 0(7), 0(14) | 0 |
| 24 | 12.5 | oral | 690(0), 20(7), 0(14) | 0 |
| 25 | 12.5 | oral | 560(0), 0(7), 0(14) | 0 |
| 30 | 12.5 | oral | 580(0), 0(7), 0(14) | 0 |
| 46 | 12.5 | oral | 420(0), 0(7), 0(14) | 0 |
| 31 | 12.5 | oral | 550(0), 220(7), 10(14) | 0 |
| 11 | 12.5 | oral | 590(0), 130(7), 40(14) | 12 |
| 17 | 12.5 | oral | 2240(0), 150(7) 20(14), 20(18) | 2 |
| 40 | 12.5 | oral | 130(0), 0(7), 0(14) | 11 |
| 9 | 12.5 | s/c | 50(0), 0(7), 10(14) | 3 |

[a] 98% effective against immature fluke at 10 mg/kg; oral route
85% effective against immature fluke at 7.5 mg/kg; oral route
49% effective against immature fluke at 5.0 mg/kg; oral route
[b] 81% effective against immature fluke at 10 mg/kg; oral route

We claim:
1. A compound selected from the group consisting of:
2,6-bis(2-hydroxy-3-bromo-5-fluorobenzyl)-4-chlorophenol;
2,6-bis(2-hydroxy-3-bromo-5-chlorobenzyl)-4-fluorophenol;
2-(2-hydroxy-3-bromo-5-fluoro-α-methylbenzyl)-6-(2-hydroxy-3-bromo-5-fluorobenzyl)-4-chlorophenol;
2,6-bis(2-hydroxy-3-bromo-5-fluorobenzyl)-4-fluorophenol;
2,6-bis(2-hydroxy-3-iodo-5-chlorobenzyl)-4-fluorophenol; or
2,6-bis(2-hydroxy-3-iodo-5-fluorobenzyl)-4-fluorophenol.

2. The compound 2,6-bis(2-hydroxy-3-bromo-5-fluorobenzyl)-4-chlorophenol.

3. The compound 2,6-bis(2-hydroxy-3-bromo-5-chlorobenzyl)-4-fluorophenol.

4. The compound 2-(2-hydroxy-3-bromo-5-fluoro-α-methylbenzyl)-6-(2-hydroxy-3-bromo-5-fluorobenzyl)-4-chlorophenol.

5. The compound 2,6-bis(2-hydroxy-3-bromo-5-fluorobenzyl)-4-fluorophenol.

6. The compound 2,6-bis(2-hydroxy-3-iodo-5-chlorobenzyl)-4-fluorophenol.

7. The compound 2,6-bis(2-hydroxy-3-iodo-5-fluorobenzyl)-4-fluorophenol.

* * * * *